United States Patent [19]

Taylor et al.

[11] Patent Number: 4,846,573

[45] Date of Patent: Jul. 11, 1989

[54] SHAPE MEMORY EFFECT ALLOY PULL WIRE ARTICULATOR FOR BORESCOPES

[75] Inventors: Geoffrey L. Taylor, Valencia; Hamid Saghatchi, Burbank, both of Calif.

[73] Assignee: Identechs Corporation, Dallas, Tex.

[21] Appl. No.: 36,788

[22] Filed: Apr. 10, 1987

[51] Int. Cl.$^4$ ............................................. G02B 23/26
[52] U.S. Cl. .................................. 356/241; 350/96.26
[58] Field of Search ...................... 356/241; 128/4, 6; 350/96.26

[56] References Cited

U.S. PATENT DOCUMENTS

| | | | |
|---|---|---|---|
| 3,557,780 | 1/1971 | Sato | 356/241 |
| 4,290,421 | 9/1981 | Siegmund | 128/6 |
| 4,601,283 | 7/1986 | Chikama | 128/4 |

Primary Examiner—Vincent P. McGraw
Assistant Examiner—S. A. Turner
Attorney, Agent, or Firm—William L. Chapin

[57] ABSTRACT

An apparatus for remotely orienting the distant tip of a flexible borescope cable to point in a desired direction utilizes a plurality of vertabrae-like annular disks disposed transversely within the hollow interior of the distal end of the flexible cable. Fine, flexible wires fabricated from a shape memory effect (SME) alloy are fixedly attached to outermost disk, and extend longitudinally backwards slidably through aligned holes in the other disks, and slidably through hollow flexible tubes rearward of the innermost of the disks. Electrical power supplied to flexible conductors at either end of each SME alloy wires from a controllable source of electrical current at the proximal end of the flexible borescope cable permits heating a selected SME alloy wire to a transition temperature which causes the wire to assume a memory length different from its length at ambient temperature, producing a tensional force on the end disk which results in a bending moment being imparted to the flexible cable enclosing the disk.

38 Claims, 3 Drawing Sheets

SHAPE MEMORY EFFECT ALLOY PULL WIRE ARTICULATOR FOR BORESCOPES

BACKGROUND OF THE INVENTION

A. Field of the Invention

The present invention relates to apparatus for remotely orienting the distant tip of a flexible borescope. More particularly, the invention relates to articulation structures for borescopes employing pull wires.

B. Discussion of Background Art

Borescopes are elongated optical devices capable of transmitting visual images to a remote observer. The devices are used to transmit images of objects near the distant end of the device to an observer at the near end of the device. This image transmitting capability permits an observer to perform a visual inspection of remote objects within the field of view of the far end of the device. Borescopes were first used to inspect the bores of guns, hence the name. Presently, bore-scopes are used to permit inspection of a large variety of objects located in remote, inaccessible or hazardous areas. Thus, they are used in such diverse applications as the inspection of turbine engines, human bodies, and nuclear reactors.

The first borescopes were essentially rigid, elongated tubular microscopes which employed a series of lenses to convey an image of an object in the field of view of a field lens at a remote end of the tube to an objective lens at the observer's end of the tube. Usually, means were also provided to illuminate the field of view of the borescope, as for example by a small lamp located near the remote end of the tube.

Most modern borescopes utilize flexible fiber-optic cables rather than lenses. The fiber-optic cables contain parallel bundles of fine transparent fibers, and transmit to one end of the cable an image of the area within the field of view of the opposite end of the cable.

Most fiber-optic borescopes have a flexible protective sheath covering the entire length of the cable. Typically, the sheath is made of a durable, abrasion resistant material such as woven metal. Also, most fiber-optic borescopes include within the sheath a second fiber-optic cable which is illuminated by a bright light source at the observer's end. The second cable transmits light to the remote end of the cable, which then illuminates the field of view of the imaging fiber-optic cable.

In a recent development in flexible borescopes, a solid state television camera is contained within a borescope tip, eliminating the need for a fiber-optic image cable. The solid state camera sensor consists of a silicon chip less than $\frac{1}{4}$" in diameter and having an array of light sensitive elements, arranged in a matrix. These devices, referred to as Charge Coupled Devices ("CCD's"), are imbedded in a borescope tip and produce a video signal capable of forming an image of objects within the field of view of the CCD. The video signal is conducted by means of electrical wires within the borescope cable to a television monitor located at the observer's end of the cable.

The tips of some fiber-optic borescopes can be remotely manipulated by an observer at the viewing end of the borescope to position the axis of the imaging fiber-optic cable at a desired orientation, thereby bringing into its field of view a desired area of interest. These remotely manipulatable fiber-optic borescopes are referred to as articulated, articulating or articulateable borescopes. By applying tension to one or more flexible wires strung through the protective sheath and attached to a pivotable member near the remote end or head of the cable, the head may be tilted at an angle to the longitudinal axis of the cable. Such borescopes can have either one or two planes of articulation. The latter type permits aiming the head of the borescope to any point in a forward directed hemisphere (or larger portion of a sphere) centered around the head end of the cable.

A variety of structures permitting the bending of the remote end of an articulated conduit by an operator at the near end of the conduit have been disclosed. Examples of such articulation structures are disclosed in the following U.S. Pat. Nos.:

Stegeman, 2,424,064, July 15, 1947, Illuminating Device

Ulrich, 3,071,161, Jan. 1, 1963, Bidirectional Flexible Segmented Tube

Bazinet, 3,162,214, Dec. 22, 1964, Flexible Tubular Structures

Stokes, 3,190,286, June 22, 1965, Flexible Viewing Probe for Stokes Endoscopic Use Maudinet, 3,301,588, Jan. 31, 1967, Remote Control Manipulation of Inaccessible Objects Marie, 3,326,620, June 20, 1967, Linked Wave Transmitting System for Light Waves Bazell, 3,572,325, Mar. 23, 1971, Flexible Endoscope Having Fluid Conduits and Control Takahashi, 3,583,393, June 8, 1971, Bendable Tube Assembly Takahashi, 3,669,098, June 13, 1972, Endotracheal Tube Fukaumi, 3,799,151, Mar. 26, 1974, Controllably Bendable Tube of an Endoscope Hosono, 3,998,216, Dec. 21, 1979, Bending Tube for Endoscope Tanaka, 4,108,211, Aug. 22, 1978, Articulated, Four-Way Bendable Tube Structure Hosono, 4,347,837, Sept. 7, 1982, Structure for Preventing the Breakage of End Portions of a Protective Covering for the Adjustable Bend Section of an Endoscope Ouchi, 4,351,323, Sept. 28, 1982, Curvable Pipe Assembly in Endoscope Sakuragi, 4,396,797, Aug. 2, 1983, Flexible Cable Sheldon, 3,060,972, Oct. 30, 1962, Flexible Tube Structure Siegmund, 4,290,421, Sept. 22, 1981, Fiberscope Wentzell, 4,575,185, Mar. 11, 1986, System for a Fiber-Optic Cable for Remote Inspection of Internal Structure of a Nuclear Steam Generator All of those articulation control structures disclosed in patents listed above which are useful for articulating flexible borescopes have a common characteristic; each of the structures employs pull wires anchored to the far end of the articulateable tube section, near the borescope tip. The wires run back through guides within the borescope cable, are longitudinally slidable within the guides, and terminate at a differential tension producing member operable by a user at the observation end of the borescope cable. A single pair of wires provides two-way articulateability in a single plane. By differentially varying the tension in the two control wires, the borescope tip can be tilted in either of two directions in a single plane. Two pairs of wires are required to provided articulateability in two perpendicular planes (four-way articulateability). The Siegmund patent discloses an improved articulation structure in which three longitudinally disposed pull wires spaced at 120 degree circumferential angles provided four-way articulateability.

Wentzell, in U.S. Pat. No. 4,575,185, Mar. 11, 1986, discloses the use of sealed, flexible chambers within a flexible tube assembly. The chambers contain fluids and are differentially pressurized to vary the buoyancy of the tube assembly in a liquid environment, thereby permitting the remote end of the tube to be bent in a desired direction. By this means, the aim point of a fiber optic inspection cable contained coaxially within the flexible tube assembly may be controlled when the assembly is inserted into a liquid filled chamber such as a nuclear steam generator.

The pull wires used by all general purpose borescope articulation structures disclosed in the prior art impose certain limitations on the performance capabilities of borescopes equipped with those articulation structures. For example, the friction between the pull wires and their enclosing guide tubes becomes troublesome when long borescope cables are required Also, the weight added to the borescope cable by the lengths of 2, 3 or 4 stout pull wires can make manipulation of long cables quite difficult. As a practical matter, the above cited problems with existing pull-wire borescope articulation structures imposes an upper limit on the length of practical articulating borescopes.

In our U.S. patent application Ser. No. 926,357 filed Oct. 31, 1983, we disclosed novel borescope articulation methods and apparatus employing shape memory effect (SME) alloy actuating elements. The SME alloy actuator mechanisms disclosed in that patent application provide a highly effective means of overcoming the limitations of prior borescope articulators The present invention was conceived of to provide a novel borescope articulation mechanism particularly well adapted to incorporation into, and modification of, existing pull-wire borescopes.

OBJECTS OF THE INVENTION

An object of the present invention is to provide means for remotely articulating the end of a flexible borescope.

Another object of the invention is to provide a borescope articulation apparatus which is useable with flexible borescopes of unlimited length.

Another object of the invention is to provide an improved borescope articulation apparatus which may be readily incorporated into the design of existing pull-wire actuated borescopes.

Various other objects and advantages of the present invention, and its most novel features, will be particularly pointed out hereinafter in connection with the appended claims.

It is to be understood that although the invention disclosed herein is fully capable of achieving the objects and providing the advantages mentioned, the structural and operational characteristics of the invention described herein are merely illustrative of the preferred embodiments. Accordingly, we do not intend that the scope of our exclusive rights and privileges in the invention be limited to the details of construction and operation described. We do intend that reasonable equivalents, adaptations and modifications of the various embodiments and alternate forms of the present invention which are described herein be included within the scope of the invention as defined by the appended claims.

SUMMARY OF THE INVENTION

Briefly stated, the present invention comprehends a novel and highly efficient apparatus for deflecting or articulating the remote tip of a flexible borescope. The apparatus is thus useful for directing the aim point of a flexible borescope to a desired direction in space.

The novel articulation mechanism according to the present invention utilizes a plurality of fine wires fabricated from a special class of metal alloys known in the art as Shape Memory Effect ("SME") alloys. Nickel-titanium ("NITINOL") alloys and copper-zinc-aluminum or copper-zinc-tin ("SME BRASS") alloys constitute the two main classes of SME alloys. When a wire fabricated from one of these alloys is heated above a certain temperature, characteristic of the particular alloy composition, the wire changes form rapidly from one shape to a different, "Memory" shape, which has been previously imprinted on the wire. The present invention preferably uses fine, flexible SME alloy wires which have a shorter length memory shape than their length at ambient temperatures. These SME alloy wires contract upon being heated above their transition temperature. Recovery of the contracted memory length is accompanied by the production of a substantial tensional force.

In a typical embodiment of the present invention, the two, three or four pull wires which in prior art pull-wire articulating borescopes are required to be slidably contained within hollow tubes or sheaths within the entire length of a borescope cable are replaced by electrical conductors which may be fixedly held within the cable. The end lengths of the pull wires which in prior art articulation mechanisms thread slidably through annular shaped, vertabrae-like disks and attach to an end disk near the junction of the flexible borescope cable with the borescope tip are replaced by fine, flexible SME alloy actuator wires. In a typical embodiment of our mechanism, the SME alloy wires are about 26 inches long. Each of the SME alloy wires are mechanically and electrically coupled at their inner ends to a separate one of the electrical conductors, and mechanically coupled at their outer ends to the end disk near the borescope tip. Hollow sleeves are provided within the far end of the borescope cable for slidably containing the lengths of the SME alloy actuator wires located inwards of the innermost vertabral disc. Typically, this length is about 24 inches. A flexible conductor is connected to the far end of each SME alloy actuator wire, and extends back through the borescope cable to provide a return path for current flowing through the actuator wire.

A controllable electrical current source at the proximal end of the borescope cable connected to each SME alloy actuator wire and the return conductor is used to resistively heat a selected SME alloy actuator wire above its transition temperature. When so heated, the SME alloy actuator wire contracts to its memory length, exerting a substantial tensional force on the end disk, and therefore on the end of the flexible borescope cable. Since the far end of each flexible SME alloy actuator wire is fastened to the end disk at a radially spaced position from the longitudinal axis of the cable, the tensional force exerted by the actuator wire causes a bending moment to be applied to the flexible end portion of the cable coaxially enclosing the end disk, causing the end portion of the cable to bend towards the heated actuator wire.

Interrupting the drive current to a heated SME alloy wire permits it to cool by convection or conduction. This relieves the internal stress in the SME alloy actuator wire which caused it to contract when the wire was heated to the transition temperature of the alloy. With the stress decreased, the wire may be forced to assume its quiesient, elongated length by an auxiliary force producing element, such as a conventional spring. Alternatively and preferably, the SME alloy actuator wire may be trained to recover a second, quiesient, elongated memory length upon being cooled below its transition temperature The use of such two-way trained SME alloy actuator wires eliminates the need for auxiliary bias springs.

DESCRIPTION OF THE PREFERRED EMBODIMENTS

Introduction

The novel borescope articulation devices according to the present invention employ pull-wire actuators made of shape-memory-effect ("SME") alloys. These alloys have some rather unusual properties. For that reason, a more complete understanding of the operation of the novel articulation devices to be described can be facilitated by a brief description of the properties of SME alloys, and is presented below.

Shape-memory-effect alloys are metals or polymers which, if plastically deformed at one temperature, will recover their original shape on being raised to a particular higher temperature, called the transition temperature. The original shape which is "remembered" by the metal upon being heated above the transition temperature is imprinted in the metal by forming the metal into that shape at a temperature far above the transition temperature.

Metal alloys displaying a shape-memory-effect suitable for our actuators include nickel-titanium (NITINOL) and copper-nickel-aluminum or copper-zinc-aluminum (SME brass). These alloys have one particular crystal structure called martensite at a temperature below the transition temperature for the particular alloy, and a different crystal structure, called austenite, above the transition temperature.

To "train" a SME alloy actuator element to remember a particular shape configuration, the element is placed in a fixture and heated to a high temperature sufficient to anneal the element, typically 500° C. to 800° C. While held at this temperature, the part is mechanically stressed by the fixture to produce a desired shape. During this operation, the metal assumes what is called the parent or beta phase. The part is subsequently cooled to a temperature at which the internal structure of the metal is transformed into an orderly crystalline state referred to as a quench induced martensitic state. The martensitic transformation starts at a temperature referred to as $M_S$, and finishes at a lower temperature referred to as $M_F$. These temperatures vary as a function of alloy composition. $M_S$ is reported to vary between $-273°$ C. for NI-TI binary alloys, and $-105°$ to $+300°$ C. for CU-ZN-AL and CU-NI-AL ternaries.

After an actuator element has been trained as described above, the element can be mechanically stressed inelastically to a deformed state having substantial residual strain. If the element is now heated to a temperature referred to as $A_S$, the internal crystal structure begins to change from martensitic to austenitic, a process which is complete at a higher temperature referred to as $A_F$. During this process, the element recovers its original "trained" shape, and may exert a substantial force in doing so. $A_S$ is above $M_S$, and the range between $A_S$ and $A_F$ may be defined as a shape memory recovery range. Typically, this range is about 20° C. to 30° C., although it has been reported to be as low as 6° C. and as high as 80° C. for certain alloy compositions.

The training process described above produces what is referred to as a one-way memory effect. SME elements having a two-way memory effect are more useful for use in some of our articulation mechanisms. In an SME alloy element having a two-way memory, the element transforms into its initially imprinted shape when its temperature is raised to $A_F$. Additionally, however, the element transforms into a second memory shape when cooled below $M_S$.

To imprint a two-way memory on an SME alloy element, the first memory shape is imprinted on the element exactly as has been described above for the one-way training process. The element is then cooled below $M_S$, mechanically stressed to a second memory state, producing what is referred to as a stress induced martensitic transformation. The part is then heated to its austenitic transition temperature ($A_S$ to $A_F$), at which time it assumes its first memory shape. Next, the part is cooled below $M_S$ while being stressed to conform to the second memory shape. This process is then cyclically repeated until memory of the second shape has been imprinted on the element. When imprinted with two-way memory, the element will assume the first memory shape when heated above the transition temperature of the alloy, and assume the second memory shape when cooled below the transition temperature.

Structures made of SME alloys have certain characteristics which are desirable for actuators in general, and for our novel borescope pull-wire articulation mechanism in particular.

A particularly important characteristic of SME alloy elements is the great force which can be exerted by the element in recovering its high temperature memory state when raised above the transition temperature. For example, the amount of force exertable by a SME alloy wire in recovering its high temperature, parent phase memory shape is typically 50,000 lbs. per square inch:

approximately 200 times the force that can be exerted by expansion and contraction of a bimetallic element of the same weight. Also, the permissible strain deformation for 100% shape recovery is much larger than ordinary metals. Thus, typical steel spring material can be deformed elastically only about 1%, while copper based SME alloys can be deformed 3-4%, and Ni-TI alloys 6% to 8%.

Another important characteristic of SME alloys which makes them desirable for our pull-wire articulators is the rapid recovery of the high temperature memory state of elements fabricated from the alloys. Typically, the propagation velocity of this change approximates the speed of sound in the material, i.e., is thousands of feet per second. A SME alloy element which has had its temperature raised above the transition temperature and recovered its high temperature memory state recovers its low temperature memory state at a generally slower rate, and with the production of much less force than when recovering its high temperature memory state. These factors must also be considered in the design of SME alloy articulators.

DETAILED DESCRIPTION

Figure 1:
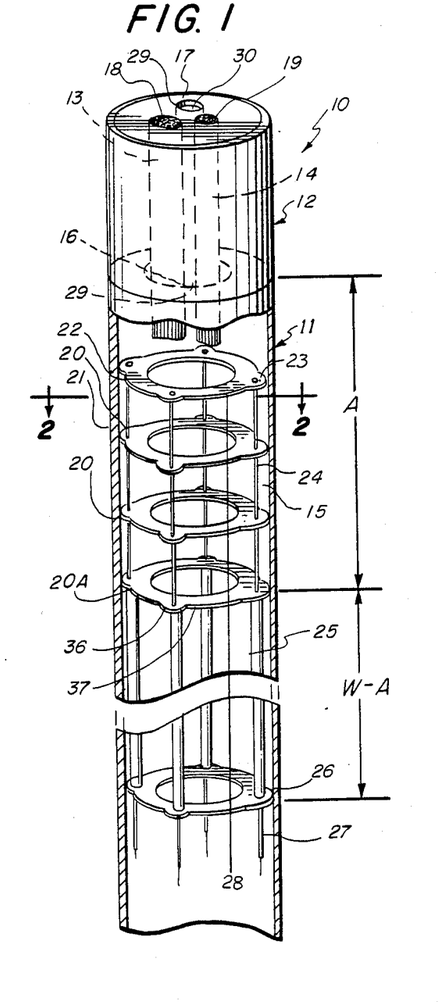
FIG. 1 is a partially sectional perspective view of an SME alloy wire borescope articulation mechanism according to the present invention.

FIG. 1 shows a basic embodiment of a pull-wire articulator for borescopes constructed according to the present invention. As was previously stated, an object of the present invention was to provide an improved borescope articulation apparatus which could be readily incorporated into the design of existing borescopes. Accordingly, the exemplary embodiment of our novel articulating borescope 10 shown in FIG. 1 employs elements in common with existing borescopes.

Referring now to FIG. 1, a borescope 10 incorporating our novel articulator design is shown to include an elongated, cylindrical flexible borescope cable 11 and a rigid cylindrical borescope tip or head 12 of approximately the same diameter as the cable attached to the forward end of the cable, in coaxial alignment therewith. A flexible, coherent fiberoptic image guide 13 and a flexible, incoherent fiber-optic light guide 14 are shown running longitudinally through a hollow interior channel 15 of the borescope cable 11. Image guide 13 and light guide 14 extend forward through the hollow interior channel 16 of tip 12, where they are fastened to a disc-shaped end plate 17 forming the front or distal face of the tip.

End plate 17 contains an entrance aperture 18 for fiber-optic image guide 13, and an exit aperture 19 for fiber-optic light guide 14. The specific details of the borescope cable and head recited above are by way of example only. It is to be understood that our novel articulation mechanism to be described below could be advantageously used for articulating other types of borescopes, such as those having an integral CCD (Charge Coupled Device) camera in the borescope head.

As shown in FIG. 1, the articulating borescope 10 includes an array of annular, vertabrae-like discs 20 disposed coaxially within the flexible jacket 21 of borescope cable 11. The discs 20 are contained within the distal end of cable 11, are disposed at regular longitudinal intervals within the cable. An outermost disc 22 is positioned at the transverse junction between tip 12 and the distal end of cable 11. The length of the borescope cable 11 containing discs 20 and 22 comprises an articulateable or bendable section designated A in FIG. 1.

As shown in FIG. 1, each disc 20 contains four holes 23 circumferentially spaced at ninety-degree intervals. In conventional pull-wire articulating borescopes, a set of four inextensible pull-wires 24 is slidably contained within a separate one of holes 23. The distal end of each pull-wire 24 is secured to the outermost disc 22 by welding or other suitable means As shown in FIG. 1, pull-wires 24 run backward from an innermost disc 20A through incompressible guide sheaths 25, within flexible cable 11, exiting the proximal end of the cable. At that location, means are provided permitting an operator to apply differential tension between pull-wires 24 forming a diametrically opposed pair. This causes the outermost annular ring 22 to tilt in a plane containing the pair of pull-wires 24, towards the wire in greater tension. Since the outermost annular ring 22 is fastened to the junction of the borescope cable 11 and the tip 12, the longitudinal axis of the tip is bent in the same direction. By manipulating the orthogonal pair tip 12 in an orthogonal direction can be effected. Simultaneously applying differential tension to the two orthogonal pairs of pull-wires 24 permits bending tip 12 in any desired direction.

As was previously mentioned, the frictional force between the pull-wires 24 and the incompressible guide sheaths 25 containing the guide wires in prior art articulating borescopes can become substantial for long borescope cables. These frictional forces impose a practical upper limit on all such pull-wire articulation mechanisms. Our novel SME alloy pull-wire articulation mechanism eliminates the above-referenced problem, and permits the construction of articulating borescopes of unlimited length, and will now be described.

Referring again to FIG. 1, our novel borescope articulation mechanism 10 is shown to have a facial similarity to conventional pull-wire articulation mechanisms. However, the SME alloy pull-wires 24 of our articulation mechanism do not extend the full length of the borescope cable 11. Instead, our pull-wires 24 and enclosing guide sheaths 25 extend a relatively short distance back from the rearmost annular disc 20A to a junction ring 26. At this junction ring, flexible electrical conductors 27 are connected to the rear end of each SME alloy pull-wire 24, and extend backwards to the proximal end of the cable. The free ends of the electrical conductors are there connected to a source of electrical current, in a manner and for the purpose to be described. The length of borescope cable 11 containing those lengths of the SME alloy pull wires 24 rearward of rearmost annular disc 20A is designated W-A in FIG. 1.

Guide sheaths 25 in our borescope 10 also differ from those used in conventional borescopes. The latter use guide sheaths made of a tightly wound helix of spring wire. The guide sheaths 25 of borescope 10 according to the present invention are made of flexible, heat resistant, electrically non-conductive tubing. Preferably, guide sheaths 25 are made of small bore teflon tubing.

While the annular rings in conventional pull-wire borescope articulation mechanisms may be made of conductive metal, the annular rings 20 for our articulation mechanism must be made of an electrically non-conductive material. Alternatively, the holes 23 through the annular rings 20 may be provided with insulating inserts, but in any event, means must be provided to keep each of the wires 24 electrically isolated from one another until they terminate in the outermost annular ring 22.

Outermost annular ring 22 is electrically conductive, and forms one node of an electrical circuit having as four branches the pull-wires 24. A flexible insulated ground conductor 28 is electrically connected to the outermost annular disc 22, and extends backward through the hollow interior channel 15 of the borescope cable 11, to exit at its proximal end.

As shown in FIG. 1, the tip 12 of borescope 10 according to the present invention includes a hollow air channel 29, communicating with the hollow interior channel 15 of the borescope cable 11, and having an exhaust outlet 30 through the disc-shaped end plate 17 of the tip.

Figures 5, 6:
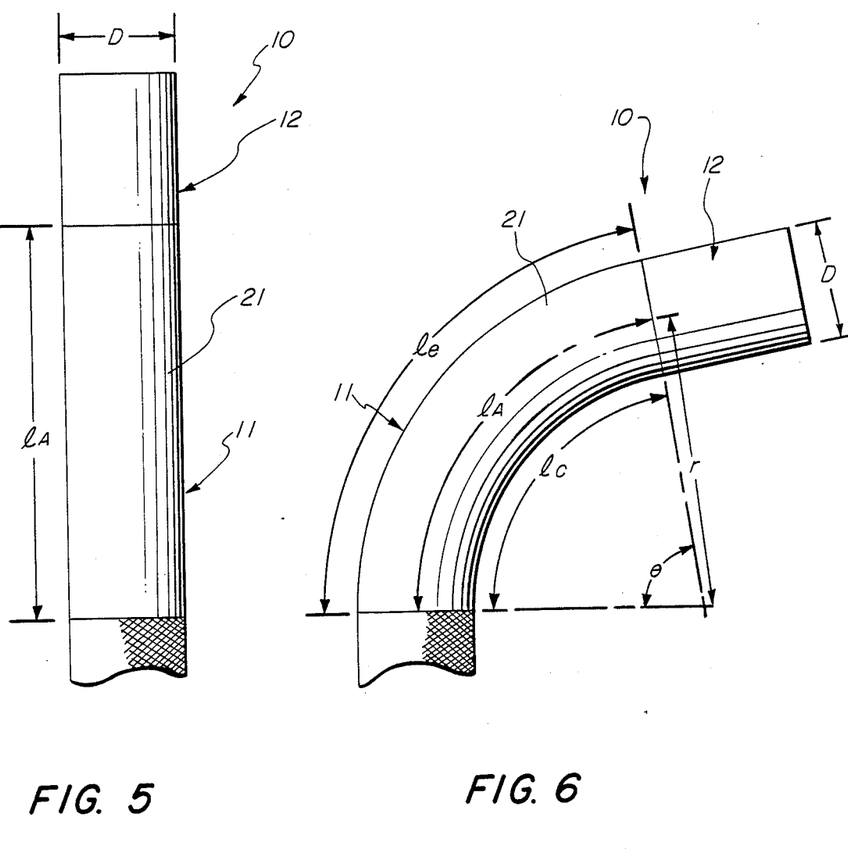
FIG. 5 is a partially diagrammatic view of part of the mechanism of FIGS. 1-4, showing how deflection angles of the mechanism are measured.
FIG. 6 is a view similar to that of FIG. 5, but showing the mechanism deflected.
Figure 7:
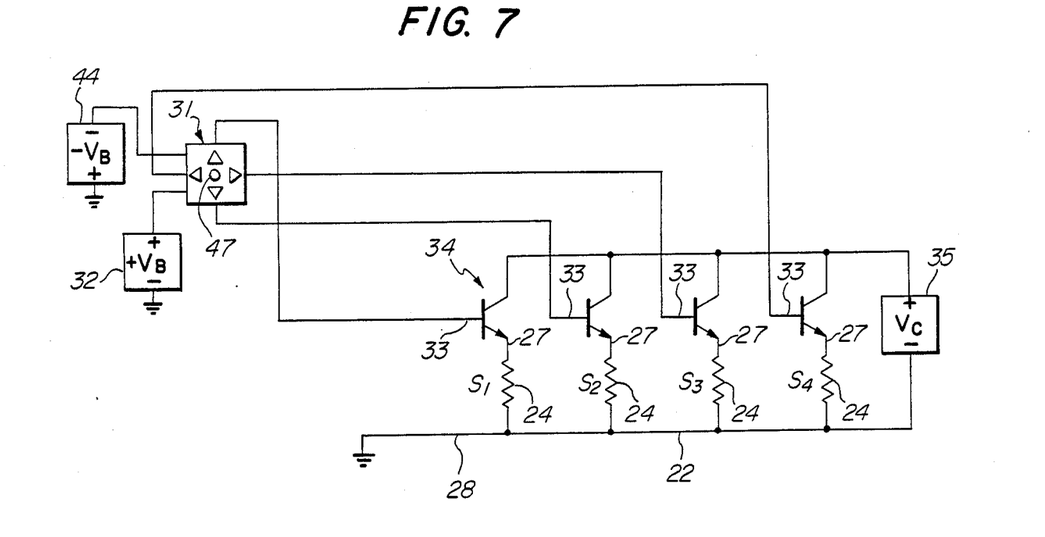
FIG. 7 is a schematic diagram of an electrical controller circuit for the apparatus of FIG. 1.

FIG. 7 illustrates in schematic form the interconnection of elements providing means for controllably heating by electrical current selected pull-wires 24. As shown in FIG. 5, a two-axis potentionmeter 31 of the joy-stick type is used to vary the amount of base drive current, from a base supply voltage source 32, inputted into the bases 33 of power transistors 34. The amount of base drive current into the base 33 of each power transistor 34 in turn varies the amount of emitter current into each pull-wire 24, supplied from collector supply voltage source 35. Operation of the means for controllably heating selected pull-wires 24 is described in greater detail below.

The pull-wires 24 of the articulating borescope 10 according to the present invention are made of a shape memory effect (SME) alloy. In one version of our novel articulating borescope 10 according to the present invention, we used SME alloy pull-wires 24 having a composition of 50% nickel, 50% titanium. This material is known in the art as NITINOL. The diameter of the pull-wires 24 used in our test was 0.016 inch. Each of the wires 24 was trained to exhibit a two-way memory, contracting upon heating the wire to the transition temperature of the NITINOL alloy, and expanding to its initial length when allowed to cool. The 50-50 NITINOL alloy used in our tests has a memory recovery temperature range extending from $A_S=$ approximately 104° F. to $A_F=$ approximately 180° F. Each NITINOL SME alloy pull-wire 24 was prepared as follows:

First, a two-feet length of 0.016" diameter 50-50 NITINOL wire was annealed at 550° C., with just enough stress placed on the wire to keep it straight during the annealing process. Thus the first memory state imprinted on the wire was a straight shape of a given length. After annealing, the wire was placed in a fixture which permitted the wire to be cyclically heated by electrical current flowing through the wire to approximately 230° F., well above $A_F$, and allowed to cool.

A second, low temperature memory shape was imprinted on the wire by placing a two-pound tension load on the wire as it cooled. Listed below are relevant parameters for imparting a two-way memory on our pull-wires 24.

Wire composition: 50% Nickel, 50% Titanium (NITINOL)
Wire Size: 0.016 inch diameter
Initial wire length: 24 inches
Training load: 2 lbs.
Wire resistance: 5.9 ohms
Supply voltage: 12 v–15 v
Heating current 2.4 amperes
Heating time 2.5 sec.
Cooling time: 38 sec.

During the memory imprinting process, the following observations were made.

| Wire State | Wire Length |
| --- | --- |
| Pre-annealing | 24 inches |
| Post-annealing (550° C. + 1 hr.) | 24¼ inches |
| Effective in training @ $T_{amb}$ = 68° F. | 24⅞ inches |
| After 60 cycles, 2-lb. load, $T_{amb}$ = 68° F. | 26⅞ inches |
| After 60 cycles, 2-lb. load, $T_H$ = 230° F. | 25⅞ inches |
| ΔL | 1 2/8 inches |
| After 1464 cycles, 2-lb. load $T_{amb}$ = 68° F. | 26⅞ inches |
| After 1464 cycles, 2-lb. load $T_H$ = 230° F. | 25⅞ inches |
| ΔL | 1 2/8 inches |
| After 1464 cycles, no-load, $T_{amb}$ = 68° F. | 26¼ inches |
| After 1464 cycles, no-load $T_H$ − 230° F. | 25¼ inches |
| ΔL | 1 inch |

From the above data, it is seen that the length difference ΔL between the first, high temperature memory state of a 24 inch SME alloy pull-wire 24 and the second, low or ambient temperature memory state of the wire is approximately 1¼ inch with a two-pound load on the wire, and approximately 1 inch with a no-load. The elongation of approximately one inch of a 24-inch pull-wire 24 upon cooling it below the contracted high-temperature, first memory state corresponds to a strain level of approximately 4 percent. Conversely, the 4 percent length reduction in a pull-wire 24 which has been heated to its first memory shape recovery temperature range of approximately 104° F. to 180° F. provides a novel and very effective means for effecting the controllable deflection or articulation of the tip 12 of borescope 10, as will now be described.

Referring now to FIG. 5, a borescope 10 according to the present invention is shown in an undeflected state, and in a deflected state in FIG. 6B. In FIG. 6, the symbols are defined as follows:

$1_a$: length of articulation joint, i.e., longitudinal distance between innermost annular disc 20 and outermost angular disc 22.
$1_w$: total length of SME alloy pull-wire 24.
D: diametrical spacing between opposite pull-wires 24.
θ: deflection angle.
$1_e$: length of pull-wire @ low-temperature within articulation joint.
$1_c$: length of pull-wire contracted @ high-temperature within articulation joint.
ΔS: pull-wire strain level.
r: radius of curvature of deflected borescope articulation joint.

1. From FIG. 6B, it may be seen that;

$$1_e = (r + D/2)\theta, \qquad \text{eqn. 1}$$

2. From the definition of strain level;

$$1_c = 1_e - \Delta S 1_w, \qquad \text{eqn. 2}$$

3. From FIG. 6;

$$1_c = (r - D/2), \qquad \text{eqn. 3}$$

Combining equations 1, 2, and 3 gives;

$$\theta = \Delta S 1_w / D \qquad \text{eqn. 4}$$

For a maximum contraction of a pull-wire 24 of 4 percent, corresponding to a strain level ΔS of 0.04, the maximum achievable deflection angle θ for a given ratio of $l_w/D$, (pull wire length/articulation joint diameter) is given by equation 4 to be:

| lw/D | θ radians | θ degrees |
|---|---|---|
| 1 | .04 | 2.29° |
| 10 | .4 | 22.9° |
| 78.53 | Π | 180.0° |
| 100 | 4.0 | 229.0° |

Our borescopes had a $l_w=24''$, and $D=5/16''$, giving a $l_w/D=76.8$, providing a maximum deflection angle of 176° degrees. Thus, with modest and reasonable values for $l_w$ and D, we were able to achieve deflection angles of nearly 180 degrees. Since a deflection angle of 180 degrees would permit a borescope tip to be aimed at any point in a spherical space surrounding the tip, a 180-degree deflection angle capability would be adequate for most purposes.

As was stated above, the SME alloy of which pull-wires 24 in a model embodiment of our borescope 10 were fabricated has a shape memory recovery temperature of approximately 100° F. to 200° F. At 100° F., the pull-wires 24 begin to contract, and are fully contracted at 200° F. The calculated time constant for heating in free air 0.016 inch diameter wires used in our tests, using a heating current of 1 to 2 amperes, is approximately 12.9 sec., giving a calculated response time to full contraction of approximately 20 seconds. In fact, we observed actuation times of approximately 10 seconds. The shorter response time is due in part to the fact that we did not have to raise the temperature of the wires all the way to 200° F. to achieve the desired actuation deflection angles. However, even the shortened, 10-second response time would be too long for typical borescope articulation requirements.

One method of decreasing the thermal time constant of cooling and heating the SME alloy actuator wires 24 is to provide means for more effectively cooling the wires, and increasing their heating rate. Thus, by using forced convection, and increased heating current, both the cooling and heating rates of the pull-wires 24 may be substantially increased. In our tests, we used air having an initial temperature of 68° F. and blowing over a pull-wire 24 at a rate of one standard cubic feet per minute (1 SCFM), and an increased heating current of 6-7 amperes. With these parameters, we observed response times of the order of 0.8 seconds, which would be adequate for most borescope articulation requirements.

Figure 3:
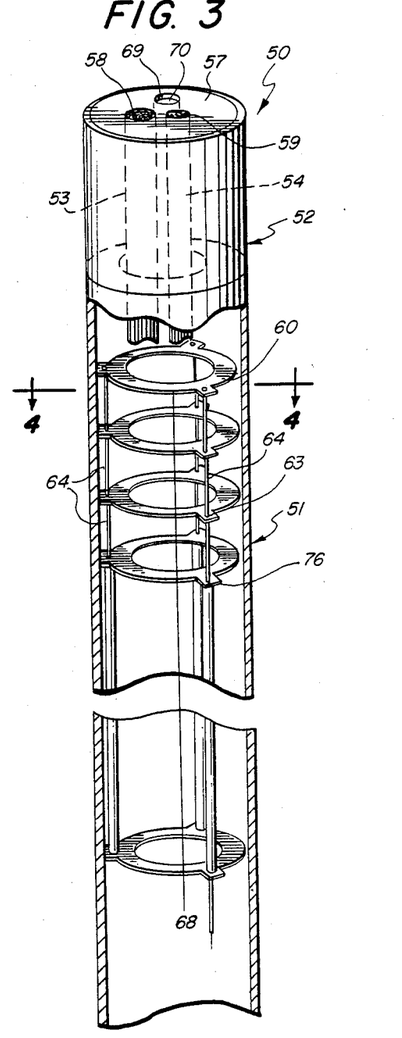
FIG. 3 is a partially sectional perspective view of another embodiment of an SME alloy wire borescope articulation mechanism according to the present invention.

Means for providing cooling air to pull-wires 24 to decrease heating and cooling times of the wires, thereby increasing articulation speed of borescope 10, is illustrated in FIGS. 1 and 3. As shown in FIGS. 1 and 3, annular discs 20 have radially outwardly projecting lugs 36 spaced at regular angles around the circumferential surface 37 of the disc. Thus, with the outer surfaces of the lugs 36 adjacent to the inner circumferential wall 38 of hollow interior channel 15 of borescope cable 11, segmented annular channels 39 are formed between the inner circumferential wall of the channel and the outer circumferential surface 37 of the disc. A source of pressurized air located at the proximal end of the borescope cable 11 and not shown in the Figures is used to blow air through segmented annular channels 39, from where the air enters the hollow interior channel 16 of borescope head 12, and exits to the atmosphere through hollow air channel 29. Air flowing through segmented annular channels 39 is in direct contact with that length of each pull-wire 24 exposed within the length of the articulating section between the innermost disc 20A and the outermost disc 22. That flowing air provides an efficient means for rapidly cooling the pull-wires. Cooling pull-wires 24 reduces the thermal time constant of the wires, and increases articulation speed.

More efficient cooling of the pull-wires 24 and accompanying further increases in response speed can be obtained by blowing cooling air through the guide sheaths 25. Alternatively, the guide sheaths may be perforated, allowing air blowing through the segmented annular channels 39 to contact the length of the pull-wires 24 contained within the guide sheaths.

Figure 4:
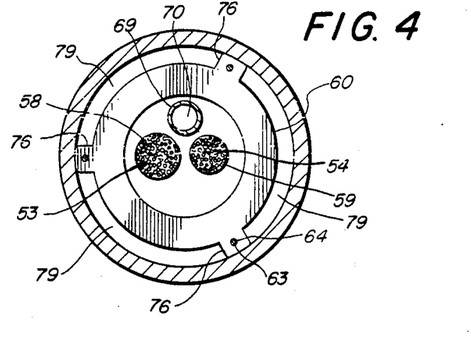
FIG. 4 is a transverse sectional view of the mechanism of FIG. 3, taken along line 3—3.

An alternate embodiment of our novel articulating borescope is shown in FIGS. 3 and 4. The embodiment 50 shown in FIGS. 3 and 4 utilizes 3 pull-wires 64 in holes 63 through lugs 76 projecting radially outward from discs 60 at 120 degree intervals. Since any radius vector can be resolved into components along three axes intersecting at 120 degrees, as well as along two axes intersecting at 90 degrees, any desired radial direction of deflection of borescope tip 52 of borescope 50 can be achieved by contracting the correct combination of the three pull-wires 64.

As previously mentioned, FIG. 7 illustrates, in schematic fashion a method of controlling the articulation of the remote tip 12 of borescope 10, from the proximal end of borescope cable 11. A detailed description of the structure and function of elements in FIG. 7 will now be given.

In FIG. 7, each of the SME alloy actuator pull-wires 24 is represented as a resistance element connected between a common return terminal 22 and through a flexible conductor 28 to the emitter terminal of a separate power transistor 34. Also in FIG. 7, the pull-wires 24 are further given a designation corresponding to their spatial location in a transverse plane of the borescope cable 11. Thus, a first pull-wire 24 is arbitrarily designated S1, corresponding to the positive Y direction in a cartesian coordinate space. The pull-wire 24 diametrically opposed to the one designated S1 is designated S2, corresponding to the negative Y direction in the same coordinate system. Similarly, the remaining pair of diametrically opposed pull-wires 24 are designated S3 and S4, corresponding to the positive and negative X directions, respectively, in the same coordinate space.

As shown in FIG. 7, the base drive signals for power transistors 34 are selectively generated by a "joy stick" controller 31.

Joy stick controller 31 comprises a pair of orthogonally positioned potentionmeters 42A and 42B responsive to orthogonal deflections of a joy stick mechanically coupled to the wipers of both potentionmeters. As shown in more detail in FIG. 8, each potentionmeter 42 has connected in parallel with its end terminals a second, trim potentionmeter 43. The wiper of each joy stick potentionmeter 42 is electrically connected to a positive voltage source 32, while the wiper of the trim potentionmeter 43 is connected to a negative voltage source 44. Thus, with the joy stick and the wiper of the joy stick potentionmeter 42 in a central, neutral position, trim potentionmeter 43 may be adjusted so that both ends of the joy stick potentionmeter are at zero potential.

Figure 8:
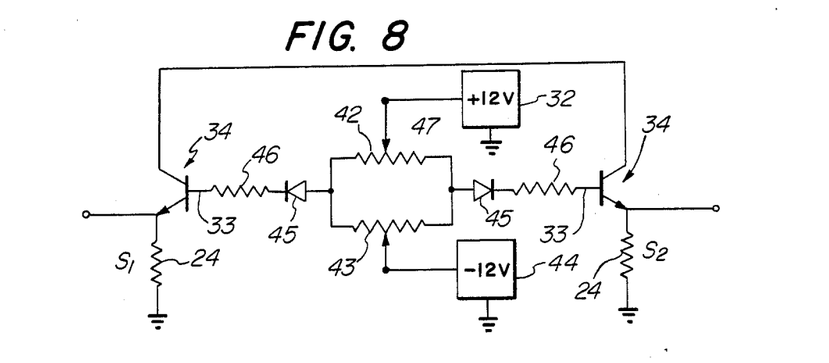
FIG. 8 is a more detailed view of a portion of the controller of FIG. 7.

As shown in FIG. 8, each end of a joy stick potentionmeter 42 is connected through a diode 45 to one terminal of a base drive resistor 46, the other terminal of which is connected to the base terminal 33 of one of the power transistors 34. Moving the joy stick handle 47 and the attached wiper of a joy stick potentionmeter 42, which is connected to a positive voltage source, towards one of the two end terminals of the potentionmeter therefore causes a variable, positive base drive voltage to be applied to the associated power transistor 34. This causes heating current to flow in the pull-wire 24 in the emitter leg of that power transistor. Moving the joy stick handle 47 from a central, neutral position to a direction having components along the sensitive axes of both potentionmeters 42A and 42B causes the appropriate pair of pull-wires 24 to heat and contract, deflecting the tip of borescope 10 in a direction corresponding to the joy stick deflection. Since the magnitude of the emitter current from power transistors 34 which flows into pull-wires 24 is proportional to the amount of deflection of the joy stick handle 47, both the magnitude and direction of deflection of the borescope tip 12 can be conveniently controlled by the mechanism described.

FIGS. 3 and 4 illustrate an alternate embodiment of an articulator according to the present invention.

As was stated previously, any position that can be expressed as a vector having cartesian coordinates along intersecting perpendicular (x and y) axes may be resolved as well into components along linear coordinate axes intersecting at 120 degrees. Therefore, the tip 52 of a borescope 50 having three SME alloy pull-wires 64 spaced at 120 degree circumferential angles from one another may also be deflected to point to any direction in space, as has been previously stated. In FIGS. 3 and 4, each element is assigned a number forty higher than the corresponding element in the four-wire mechanism shown in FIGS. 1 and 2.

Figure 2:
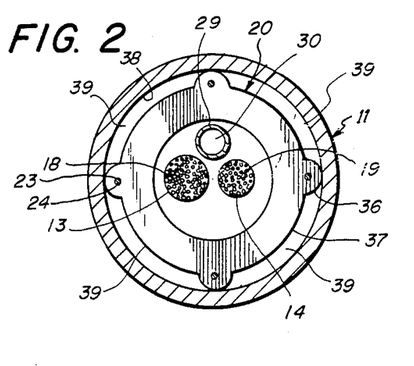
FIG. 2 is a transverse sectional view of the mechanism of FIG. 1, taken along line 2—2.

Thus, the three-lug discs in FIGS. 3 and 4 are given the element number 60, compared to the four-lug discs 20 in FIGS. 1 and 2, etc.

Figure 9:
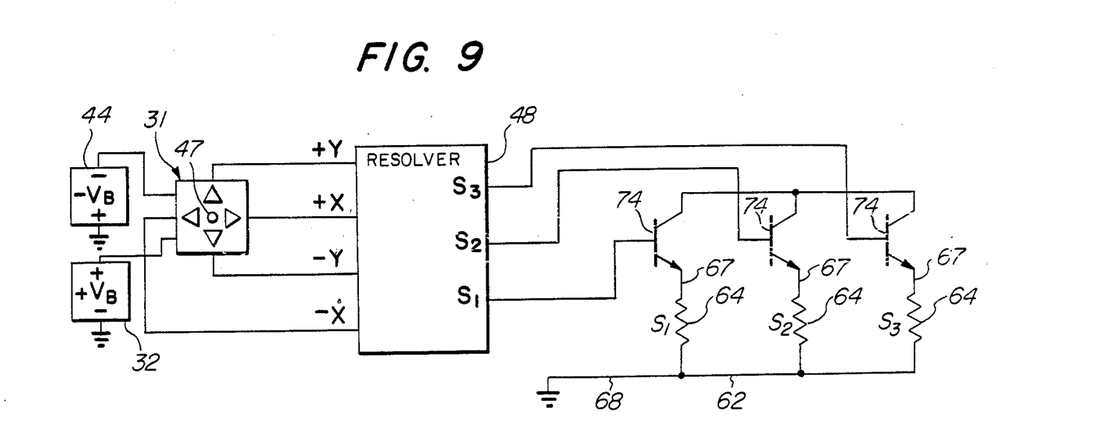
FIG. 9 is a schematic diagram of an electrical controller circuit for the apparatus of FIG. 3.

A conventional cartesian joy stick controller 31 may also be used to generate the drive signals required for the three-wire borescope 50. As shown in FIG. 9, generation of drive signals for actuators aligned with coordinate axes 120 degrees apart may be accomplished by interposing a resolver 48 between the cartesian joy stick controller 31 and three-axis, or "Y" configuration borescope 50. The mechanization of resolver 48 is well within the capabilities of those skilled in the art.

What is claimed is:

1. An apparatus for controllably deflecting the remote end of a flexible borescope cable to point in an arbitrary desired spatial orientation, said apparatus comprising:
   (a) at least one annular-shaped disk transversely disposed within said cable near its distal end, and fitting snugly therewithin;
   (b) at least one elongated flexible wire fabricated of a shape memory effect alloy, the distal end of said SME alloy wire being fastened to said disk, said SME allow wire being disposed longitudinally and slidably within said cable, the proximal end of said SME alloy wire being fastened in a fixed longitudinal position to said cable; and
   (c) means for varying from an ambient value the temperature of said SME alloy wire to approach a transition temperature at which said wire assumes a length different from its ambient length, said length difference being proportional to the closeness of the actual temperature of said wire to its transition temperature, thereby producing a differential tension on said disk and causing a bending moment to be imparted to the distal end of said flexible cable, the magnitude of said bending moment being proportional to the closeness of the actual temperature of said wire to its transition temperature.

2. The apparatus of claim 1 wherein said SME alloy wire is further defined as having a first memory length for temperatures above a first transition temperature characteristic of the composition of the SME alloy of which said SME alloy wire is fabricated 3. The apparatus of claim 2 wherein said SME alloy wire is further defined as having a second memory length for temperatures below a second transition temperature characteristic of the composition of the SME alloy of which said SME alloy wire is fabricated.

4. The apparatus of claim 1 wherein said means for varying from an ambient value the temperature of said SME alloy wire comprises:
   (a) means for electrically heating said SME alloy wire; and
   (b) means for cooling said SME alloy wire.

5. The apparatus of claim 4 wherein said means for electrically heating said SME alloy wire is further defined as means for providing a flow of electrical current through said SME alloy wire.

6. The apparatus of claim 5 wherein said means for cooling said SME alloy wire includes a thermally conductive material in contact with said SME alloy wire and a lower temperature body.

7. The apparatus of claim 6 further including a source of thermally conductive fluid in thermal contact with said SME alloy wire.

8. The apparatus of claim 7 wherein said thermally conductive fluid is further defined as air flowing in contact with said SME alloy wire.

9. An apparatus for controllably deflecting the remote end of a flexible borescope cable having an elongated hollow interior channel to point in an arbitrary desired spatial orientation, said apparatus comprising:
   (a) at least one, first annular-shaped disk disposed coaxially and transversely within said cable near the distal end of said cable, said disk fitting snugly within said hollow interior channel of said cable;
   (b) at least one first elongated flexible wire fabricated of a shape memory effect alloy, the distal end of said SME alloy wire being fastened perpendicularly to said disk, said SME alloy wire extending longitudinally backwards from the rear transverse surface of said annular-shaped disk and slidably contained within a hollow flexible tube disposed longitudinally within said flexible cable, near the inner circumferential surface of said cable, the proximal end of said SME alloy wire extending from the proximal end of said hollow flexible tube and fastened in a longitudinally fixed position with respect to said cable;
   (c) a flexible insulated power conductor electrically connected to the proximal end of said SME alloy wire and running back through said flexible cable to exit at its proximal end; and
   (d) a flexible insulated ground conductor electrically connected to the distal end of said SME alloy wire and running back through said flexible cable to exit at its proximal end, whereby a controllable source of electrical current may be connected to the proximal ends of said flexible power conductor and said flexible ground conductor, thereby causing controllable ohmic heating of said SME alloy wire to approach a transition temperature causing said SME alloy wire to assume a memory length different from its ambient temperature length, said length difference being proportional to the closeness of the actual temperature of said wire to its transition temperature, and thereby producing a differential tension in said SME alloy wire causing a bending moment to be imparted to the distal end of said flexible cable, the magnitude of said bending moment being proportional to the closeness of the actual temperature of said SME alloy wire to its transition temperature.

10. The apparatus of claim 9 further including a second elongated flexible wire fabricated of an SME alloy, said second SME alloy wire being fastened perpendicularly to said disk in a position diametrically opposed to the fastening point of said first SME alloy wire, said second SME alloy wire slidably contained within a second hollow flexible tube parallel to said first hollow flexible tube, the proximal end of said second SME alloy wire being electrically connected to a second flexible insulated conductor exiting the proximal end of said flexible cable, and the distal end of said second SME alloy wire being electrically connected to said flexible insulated ground conductor, whereby said second SME alloy wire may be electrically heated to cause a second bending moment to be imparted to said distal end of said flexible cable in the same plane as, but in an opposite direction to, said first bending moment.

11. The apparatus of claim 10 further comprising a third and fourth SME alloy wire fastened perpendicularly to said disk in positions diametrically opposed to one another at ninety degree circumferential positions with respect to said first and second SME alloy wires, said third and fourth SME alloy wires being slidably contained within third and fourth hollow flexible tubes parallel to and similar to said first and second hollow flexible tubes, the proximal ends of said third and fourth SME alloy wires being electrically connected to a second and third flexible insulated conductor, respectively, and the distal ends of said third and fourth SME alloy wires being electrically connected to said flexible insulated ground conductor, whereby said third or fourth SME alloy wire may be electrically heated to cause a third or fourth bending moment to be imparted to said distal end of said flexible cable in opposite directions both in a plane perpendicular to that of said first and second bending moments.

12. The apparatus of claim 11 further comprising means for flowing a cooling fluid in contact with said SME alloy wires.

13. The apparatus of claim 11 wherein said SME alloy wires are further defined as having a second memory length for temperatures below a second transition temperature characteristic of the SME alloy of which said SME alloy wire is fabricated.

14. The apparatus of claim 9 further including a second elongated flexible wire fabricated of an SME alloy, said second SME alloy wire being fastened perpendicularly to said disk at a one-hundred and twenty degree circumferential angle from said first SME alloy wire and slidably contained within a second hollow flexible tube parallel to said first hollow flexible tube, the proximal end of said second SME alloy wire being electrically connected to a second flexible insulated conductor exiting the proximal end of said flexible cable, and the distal end of said second SME alloy wire being electrically connected to said flexible insulated ground conductor, whereby said second SME alloy wire may be electrically heated to cause a second bending moment to be imparted to said distal end of said flexible cable in a plane displaced one-hundred and twenty degrees from the plane of action of said first bending moment.

15. The apparatus of claim 14 further including a third elongated flexible SME alloy wire, third hollow flexible tube, and third flexible insulated conductor displaced circumferentially one-hundred and twenty degrees from said first and second corresponding elements, respectively, but similar in structure and formation thereto, whereby heating said third SME alloy wire causes a third bending moment to be imparted to said distal end of said flexible cable in plane displaced one-hundred and twenty degrees from the planes of action as said first and second bending moments.

16. The apparatus of claim 15 further comprising means for flowing cooling fluid in contact with said SME alloy wires.

17. The apparatus of claim 15 wherein said SME alloy wires are further defined as having a second memory length for temperatures below a second transition temperature characteristic of the SME alloy of which said SME alloy wire is fabricated.

18. An apparatus for controllably deflecting the remote end of a flexible borescope cable having an elongated hollow interior channel to point in an arbitrary desired spatial orientation said apparatus comprising:
(a) an annular-shaped end disk disposed coaxially and transversely within said cable near the distal end of said cable, said end disk fitting snugly within said hollow interior channel of said cable;
(b) a plurality of annular-shaped intermediate disks disposed coaxially and transversely within said hollow interior channel of said cable and fitting snugly therewithin, at longitudinally spaced intervals rearward of said end disk;
(c) a first elongated flexible wire fabricated of a shape memory effect alloy, said first SME alloy wire being fixedly attached to said end disk and extending longitudinally rearward therefrom slidably through aligned holes provided through the thickness dimension of said intermediate annular disks;
(d) a first hollow, flexible tube disposed longitudinally rearward of the rearmost of said intermediate disks within said hollow interior channel of said flexible cable and fixed thereto, the bore of said hollow flexible tube slidably receiving a proximal portion of said SME alloy wire;
(e) means for fixing against longitudinal movement the proximal end of said SME alloy wire;
(f) a flexible insulated power conductor electrically connected to the proximal end of said SME alloy wire and running back through said flexible cable to exit at the proximal end of said cable; and
(g) a flexible insulated ground conductor electrically connected to the distal end of said SME alloy wire and running back through said flexible cable to exit at the proximal end of said cable, whereby a controllable source of electrical power may be connected to the proximal ends of said flexible power conductor and said flexible ground conductor, thereby causing controllable ohmic heating of said SME alloy wire to approach a transition temperature causing said SME alloy wire to assume a memory length different from its ambient temperature length, said length difference being proportional to the closeness of the actual temperature of said wire to its transition temperature, and thereby producing a differential tension in said SME alloy wire causing a bending moment to be imparted to the distal end of said flexible cable, the magnitude of said bending moment being proportional to the closeness of the actual temperature of said SME alloy wire to its transition temperature.

19. The apparatus of claim 18 further including a second SME alloy wire fixedly attached to said end disk at a point diametrically opposed to the attachment point of said first SME alloy wire to said end disk, said second SME alloy wire extending longitudinally rearward from said end disk slidably through aligned holes provided through the thickness dimension of said intermediate disks at positions diametrically opposed to said holes provided for said first SME alloy wire, the proximal portion of said second SME alloy wire being slidably contained within a second hollow flexible tube similar in structure and function to said first hollow flexible tube but positioned in a parallel, diametrically opposed position thereto, the proximal end of said second SME alloy wire being electrically connected to a second flexible insulated power conductor running back through said flexible cable to exit at the proximal end of said cable, and the distal end of said second SME alloy wire being electrically connected to said flexible ground conductor, whereby said second SME alloy wire may be electrically heated to cause a second bending moment to be imparted to said distal end of said flexible cable in the same plane as, but in an opposite direction to, said first bending moment.

20. The apparatus of claim 19 further comprising third and fourth SME alloy wires fixedly attached to said end disk in positions diametrically opposed to one another at ninety degree circumferential positions with respect to said first and second SME alloy wires, said third and fourth SME alloy wires extending longitudinally rearward from said end disk slidably through aligned holes provided through the thickness dimension of said intermediate disks at positions diametrically opposed to one another at ninety degree positions with respect to said first and second SME alloy wires, the proximal portions of said third and fourth SME alloy wires being slidably contained within second and third hollow flexible tubes, respectively, identical in structure and function to said first and second hollow flexible tubes but positioned at ninety degrees with respect thereto, the proximal ends of said third and fourth SME alloy wires being electrically connected, respectively, to third and fourth flexible insulated power conductors running back through said flexible cable to exit at the proximal end of said cable, and the distal ends of said third and fourth SME alloy wires being electrically connected to said flexible ground conductor, whereby said third or fourth SME alloy wire may be electrically heated to cause a third or fourth bending moment to be imparted to said distal end of said flexible cable in opposite directions both in a plane perpendicular to that of said first and second bending moments.

21. The apparatus of claim 20 further comprising means for flowing cooling air in contact with said SME alloy wires.

22. The apparatus of claim 21 wherein said means for flowing cooling air in contact with said SME alloy wires comprises (a) an exhaust channel communicating with the exterior of said flexible cable and said hollow interior channel of said cable; and
(b) a source of pressurized air communicating with a proximal opening of said hollow interior channel of said flexible cable.

23. The apparatus of claim 22 further comprising perforations through the walls of said hollow flexible tubes permitting cooling air to contact said SME alloy wires therewithin.

24. The apparatus of claim 21 wherein said means for flowing cooling air in contact with said SME alloy wires comprises in combination:
(a) lugs projecting radially outwards from the plane of said end disk and each of said intermediate disks, each of said lugs being positioned symmetrically about a hole for an SME alloy wire, the outer transverse surface of said lug contacting the inner circumferential wall of said hollow interior channel of said flexible cable, thereby defining a plurality of longitudinally disposed, annular spaces between adjacent ones of said lugs, the outer circumferential surface of said disks, and the inner circumferential wall surface of said hollow interior channel of said cable;
(b) an exhaust channel communicating with the exterior of said flexible cable and the distal portion of said hollow interior channel forward of the outer face of said end disk; and
(c) a source of pressurized air communicating with a proximal opening of said hollow interior channel of said flexible cable.

25. The apparatus of claim 24 further comprising perforations through the walls of said hollow flexible tubes permitting cooling air to contact said SME alloy wires therewithin.

26. The apparatus of claim 25 wherein said SME alloy wires are further defined as having a second memory length for temperatures below a second transition temperature characteristic of the SME alloy of which said SME alloy wire is fabricated.

27. The apparatus of claim 18 further comprising means for controllably and selectably introducing current into a conductor pair consisting of a said flexible insulated power conductor and said flexible ground conductor for heating to a desired temperature a selected one of said SME alloy wires, said means comprising:
(a) a source of electrical current;
(b) amplifying means connected in series with said source of electrical current, said flexible power conductor, and said flexible ground conductor; and
(c) means for controlling by an external command signal the output current of said amplifying means.

28. The apparatus of claim 27 further comprising means for generating a signal responsive to the temperature of said SME alloy wires and means for varying the output current of said amplifying means in response to said temperature responsive signal.

29. The apparatus of claim 18 further including a second SME alloy wire fixedly attached to said end disk at a point measured circumferentially one-hundred and twenty degrees from said first SME alloy wire, said second SME alloy wire extending longitudinally rearward from said end disk slidably through aligned holes provided through the thickness dimension of said intermediate disks, that length of said second SME alloy wire rearward of the rearmost of said intermediate disc and being slidably contained within a second hollow flexible tube similar in structure and function to said first hollow flexible tube, the proximal end of said second SME alloy wire being electrically connected to a second flexible insulated power conductor running back through said flexible cable to exit at the proximal end of said cable, and the distal end of said second SME alloy wire being electrically connected to said flexible ground conductor, whereby said second SME alloy wire may be electrically heated to cause a second bending moment to be imparted to said distal end of said flexible cable in a plane displaced one-hundred and twenty degrees from the plane of action of said first bending moment.

30. The apparatus of claim 29 further including a third flexible SME alloy wire, third hollow flexible tube, and third flexible insulated conductor displaced circumferentially one-hundred and twenty degrees from said first and second corresponding elements, respectively, but similar in structure and function thereto, whereby said third SME alloy wire may be electrically heated to cause a third bending moment to be imparted to said distal end of said flexible cable in a plane displaced one-hundred and twenty degrees from the plane of action of said first and second bending moments.

31. The apparatus of claim 30 further comprising means for flowing cooling air in contact with said SME alloy wires.

32. The apparatus of claim 31 wherein said means for flowing cooling air in contact with said SME alloy wires comprises:
   (a) an exhaust channel communicating with the exterior of said flexible cable and said hollow interior channel of said cable; and
   (b) a source of pressurized air communicating with a proximal opening of said hollow interior channel of said flexible cable.

33. The apparatus of claim 32 further comprising perforations through the walls of said hollow flexible tubes permitting cooling air to contact said SME alloy wires therewithin.

34. The apparatus of claim 31 wherein said means for flowing cooling air in contact with said SME alloy wires comprises in combination:
   (a) lugs projecting radially outwards from the plane of said end disk and each of said intermediate disks, each of said lugs being positioned symmetrically about a hole for an SME alloy wire, the outer transverse surface of said lug contacting the inner circumferential wall of said hollow interior channel of said flexible cable, thereby defining a plurality of longitudinally disposed, annular spaces between adjacent ones of said lugs, the outer circumferential surface of said disks, and the inner circumferential wall surface of said hollow interior channel of said cable;
   (b) an exhaust channel communicating with the exterior of said flexible cable and the distal portion of said hollow interior channel forward of the outer face of said end disk; and
   (c) a source of pressurized air communicating with a proximal opening of said hollow interior channel of said flexible cable.

35. The apparatus of claim 34 further comprising perforations through the walls of said hollow flexible tubes permitting cooling air to contact said SME alloy wires therewithin.

36. The apparatus of claim 34 wherein said SME alloy wires are further defined as having a second memory length for temperatures below a second transition temperature characteristic of the SME alloy of which said SME alloy wire is fabricated.

37. The apparatus of claim 30 further comprising means for controllably and selectably introducing current into a conductor pair consisting of a said flexible insulated power conductor and said flexible ground conductor for heating to a desired temperature a selected one of said SME alloy wires, said means comprising:
   (a) a source of electrical current;
   (b) an amplifying means connected in series with said source of electrical current, said flexible power conductor, and said flexible ground conductor; and
   (c) means for controlling by an external command signal the output current of said amplifying means.

38. The apparatus of claim 37 further comprising means for generating a signal responsive to the temperature of said SME alloy wires and means for varying the output current of said amplifying means in response to said temperature responsive signal.

* * * * *